United States Patent [19]

Maurer et al.

[11] 4,168,305
[45] Sep. 18, 1979

[54] COMBATING PESTS WITH S-ALKYL-N-CARBONYL-ALKANEDITHIO-PHOSPHONIC ACID ESTER-AMIDES

[75] Inventors: Fritz Maurer; Hans-Jochem Riebel, both of Wuppertal; Rolf Schröder, Velbert; Ingeborg Hammann, Cologne; Bernhard Homeyer, Leverkusen; Wolfgang Behrenz, Overath, all of Fed. Rep. of Germany

[73] Assignee: Bayer Aktiengesellschaft, Leverkusen, Fed. Rep. of Germany

[21] Appl. No.: 867,261

[22] Filed: Jan. 5, 1978

[30] Foreign Application Priority Data

Jan. 19, 1977 [DE] Fed. Rep. of Germany ....... 2702049

[51] Int. Cl.² .................. A01N 9/36; C07F 9/02; C07C 153/09; C07F 9/44
[52] U.S. Cl. .................. 424/211; 260/938; 260/455 P; 424/212
[58] Field of Search .................. 260/938, 455 P; 424/211

[56] References Cited

U.S. PATENT DOCUMENTS 2,494,283  1/1950  Canaday ............... 260/943
4,001,404  1/1977  Hoffmann et al. ............ 260/938

FOREIGN PATENT DOCUMENTS 2014027  12/1970  Fed. Rep. of Germany .......... 260/938

Primary Examiner—Elbert L. Roberts
Assistant Examiner—Robert C. Whittenbaugh
Attorney, Agent, or Firm—Sprung, Felfe, Horn, Lynch & Kramer

[57] ABSTRACT

S-Alkyl-N-carbonyl-alkanedithiophosphonic acid ester-amides of the formula

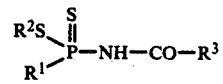

in which
  $R^1$ and $R^2$ each independently is alkyl, and
  $R^3$ is alkoxy, alkoxyalkoxy, alkylthio, alkenyloxy, alkynyloxy, aralkoxy, aryloxy, amino, monoalkylamino, dialkylamino, monoalkenylamino or arylamino, which possess arthropodicidal and nematicidal properties.

9 Claims, No Drawings

COMBATING PESTS WITH S-ALKYL-N-CARBONYL-ALKANEDITHIOPHOSPHONIC ACID ESTER-AMIDES

The present invention relates to and has for its objects the provision of particular new S-alkyl-N-carbonyl-alkanedithiophosphonic acid ester-amides which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

It is already known that dithiophosphoric acid esters and mono- and di-thiophosphoric acid diester-amides, for example, O,O-dimethyl-S-(N-methylcarbamoylmethyl)-dithiophosphoric acid ester, O,S-dimethyl-N-acetyl-thiophosphoric acid diester-amide, O-ethyl- and O-n-propyl-S-(1-carbethoxy-1-ethylthio-methyl)-N-iso-propyl-thionothiolphosphoric acid diester-amide and O-ethyl-S-(1-carbethoxy-1-ethylthiomethyl)-N-sec.-butyl-thiolphosphoric acid diester-amide, are distinguished by an insecticidal, acaricidal and nematicidal activity (see U.S. Pat. No. 2,494,283, and German Offenlegungsschriften (German Published Specification) No. 2,014,027 and U.S. application Ser. No. 631,264, filed Nov. 11, 1975, now pending).

The present invention now provides, as new compounds, the substituted dithiophosphonic acid ester-amides of the general formula

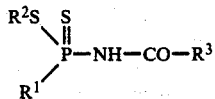
(I)

in which
R¹ and R², which may be identical or different, each represent alkyl and
R³ represents alkoxy, alkoxyalkoxy, alkylthio, alkenyloxy, alkynyloxy, aralkoxy, aryloxy, amino, monoalkylamino, dialkylamino, monoalkenylamino or arylamino.

Preferably, R¹ represents straight-chain or branched alkyl with 1 to 5 (especially 1 to 3) carbon atoms, R² represents straight-chain or branched alkyl with 1 to 6 (especially 1 to 4) carbon atoms and R³ represents straight-chain or branched alkoxy or alkylthio with 1 to 6 (especially 1 to 4) carbon atoms, straight-chain or branched alkenyloxy or alkynyloxy each with up to 6 (especially with up to 4) carbon atoms, alkoxyalkoxy with 1 to 3 carbon atoms in each alkoxy moiety, phenyloxy, halogenophenoxy (especially chlorophenoxy), benzyloxy, straight-chain or branched monoalkylamino with 1 to 6 (especially 1 to 4) carbon atoms, dialkylamino with 1 or 2 carbon atoms per alkyl radical, and phenylamino which is optionally monosubstituted or polysubstituted by chlorine.

Surprisingly, the substituted dithiophosphonic acid ester-amides according to the invention exhibit a better insecticidal, acaricidal and nematicidal action than the corresponding previously known dithiophosphoric acid esters and mono- and di-thiophosphoric acid diester-amides of analogous structure and of the same type of action. The products according to the present invention thus represent a genuine enrichment of the art.

The invention also provides a process for the preparation of a substituted dithiophosphonic acid ester-amide of the formula (I), in which a dithiophosphonic acid ester isocyanate of the general formula

(II), in which
R¹ and R² have the above-mentioned meanings, is reacted with an alcohol, mercaptan or amine of the general formula $$HR^3 \quad (III),$$

in which
R³ has the above-mentioned meaning, if appropriate in the presence of a diluent, which term includes a solvent.

If, for example, S-methyl-ethanedithiophosphonic acid ester isocyanate and diethylamine are used as starting materials, the course of the reaction can be represented by the following equation:

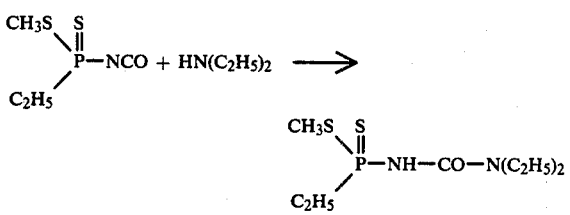

The Dithiophosphonic acid ester isocyanates (II) to be used as starting materials are known and can be prepared in accordance with customary processes, by reacting the known dithiophosphonic acid ester-amides (see Belgian Patent Specification No. 737,485) with phosgene to give the corresponding isocyanates.

The following may be mentioned individually as examples thereof: S-methyl-, S-ethyl-, S-n-propyl-, S-iso-propyl-, S-n-butyl-, S-sec.-butyl-, S-iso-butyl- and S-tert.-butyl-methane-, -ethane-, -n-propane- or -iso-propane-dithiophosphonic acid ester isocyanate.

The alcohols, mercaptans and amines (III) also to be used as starting materials are known and can also be easily manufactured industrially.

The following may be mentioned as individual examples thereof: methanol, ethanol, n- or iso-propanol, n-, sec.-, iso- or tert.-butanol, methylmercaptan, ethylmercaptan, n- or iso-propylmercaptan, n-, sec.-, iso- or tert.-butylmercaptan, prop-1-en-3-ol, prop-1-yn-3-ol, but-1-yn-3-ol, methoxymethanol, ethoxymethanol, n-propoxymethanol, isopropoxymethanol, 2-methoxyethanol, 2-ethoxyethanol, 2-n-propoxyethanol, 2-iso-propoxyethanol, phenol, benzyl alcohol, 2-chlorophenol, 4-chlorophenol, 3-chlorophenol, 2,4-dichlorophenol, 2,4,6-trichlorophenol, monomethylamine, monoethylamine, mono-n-propylamine, mono-iso-propylamine, mono-n-butylamine, mono-sec.-butylamine, mono-iso-butylamine, dimethylamine, diethylamine, aniline, 2-chloroaniline, 3-chloroaniline, 4-chloroaniline, 2,3- dichloroaniline, 2,4-dichloroaniline, 3,4;1-dichloroaniline, 3,5-dichloroaniline and 2,4,5-trichloroaniline.

The process for the preparation of the compounds according to the invention is preferably carried out in the presence of a suitable solvent or diluent. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

In certain cases, an excess of the alcohol, mercaptan or amine (III) to be used may also be employed as a solubilizing agent.

The reaction temperature can be varied within a substantial range. In general, the reaction is carried out at from 0° to 60° C., preferably at from 20° to 40° C.

In general, the reaction is allowed to take place under normal pressure.

To carry out the process, the starting materials are preferably employed in stoichiometric amounts. An excess of one or the other component produces no significant advantages. The reactants are combined in one of the above-mentioned solvents and stirred for one or more hours to complete the reaction. The mixture is worked up in the usual manner by distilling off the solvent.

According to another preferred embodiment, the intermediate isolation of the dithiophosphonic acid ester isocyanates to be employed is dispensed with and the reaction solution is employed directly.

The new compounds are usually obtained in the form of oils, which in some cases cannot be distilled without decomposition, but can be freed from the last volatile constituents by so-called "slight distillation", that is to say by prolonged heating under reduced pressure to moderately elevated temperatures, and can be purified in this way. They are characterized by the refractive index. However, some of the compounds are obtained in the crystalline form; they are characterized by their sharp melting point.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus*, *Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis*, *Periplaneta americana*, *Leucophaea maderae*, *Blattella germanica*, *Acheta domesticus*, Gryllotalpa spp., *Locusta migratoria migratorioides*, *Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius*, *Piesma quadrata*, *Climex lectularius*, *Rhodinius prolixus* and Triatoma spp.;

from the order of the Homoptera, for example *Aleurodes brassicae*, *Bemisia tabaci*, *Trialeurodes vaporariorum*, *Ahis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata legens*, *Aonidiella aurantii*, *Aspidiotus hederae*, Pseudococcus spp. and Psylla spp.;

from the order of the Lepidoptera, for example *Pectinophora gossypiella*, *Bupalus piniarius*, *Chemimatobia brumata*, *Lithocolletis blancardella*, *Hyponomeuta padella*, *Plutella maculipennis*, *Malacosoma neustria*, *Euproctis chrysorrhoea*, Lymantria spp., *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia keuhniella*, *Galleria mellonella*, *Cacoecia podana*, *Capua reticulana*, *Choristoneura fumiferana*, *Clysia ambiguella*, *Homona magnanima* and *Trotrix viridana;* from the order of the Coleoptera, for example *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolontha*, *Amphimallon solstitialis* and *Costelytra zealandica;* from the order of the Hymenoptera, for example Diprion spp., Hoplocampa spp., Lasius spp., Monomorium pharaonis and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, *Oscinella frit*, Phorbia spp., *Pegomyia hyoscyami*, *Ceratitis capitata*, *Dacus oleae* and *Tipula paludosa;* from the order of the Siphonaptera, for example *Xenopsylla cheopis* and *Ceratophyllus* spp.;

from the class of the Arachnida, for example *Scorpio maurus* and *Latrodectus mactans*;

from the order of the Acarina, for example *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp. and *Tetranychus* spp..

The plant-parasitc nematodes include *Pratylenchus* spp., *Radopholus similis*, *Ditylenchus dipsaci*, *Tylenchulus semipenetrans*, *Heterodera* spp., *Meloidogyne* spp., *Aphelenchoides* spp., *Longidorus* spp., *Xiphinema* spp., and *Trichodorus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as hightly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfontes, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. arthropods and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

(a) 1st reaction stage:

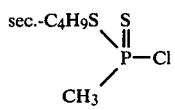

(i)

Method A

A mixture of 225 g (2.5 mol) of sec.-butylmercaptan and 200 g (2.5 mol) of pyridine was added dropwise over the course of 30 minutes, while stirring, to a solution of 292.4 g (2.5 mol) of methyldichlorophosphine in 1,600 ml of dry toluene at −20° C. The mixture was then stirred for a further 30 minutes at −20° C., and was brought to room temperature in the course of one hour. 80 g (2.5 mol) of finely powdered flowers of sulphur were then introduced into the mixture at 30° C., and the latter was warmed for 1 hour to 90° C. and then boiled for 30 minutes under reflux. After cooling to 25° C., the residue was filtered off, the filtrate was concentrated on a rotary evaporator under reduced pressure and the residue was distilled. 240 g (47% of theory) of S-sec.-butyl-methanedithiophosphonic acid ester chloride having a boiling point of 95° C./4 mm Hg remained.

Method B

A mixture of 9 g (0.1 mol) of sec.-butylmercaptan and 10.1 g (0.1 mol) of triethylamine was added dropwise at 10° C., while stirring, to a solution of 14.8 g (0.1 mol) of methanethionophosphonic acid dichloride in 150 ml of toluene. The reaction solution was then warmed for 2 hours to 90° C., after which it was cooled to room temperature and filtered, the filtrate was concentrated on a rotary evaporator under reduced pressure and the residue was distilled. 16 g (80% of theory) of S-sec.-butylmethanedithiophosphonic acid ester chloride of boiling point 95° C./4 mm Hg remained.

The following compounds of the formula

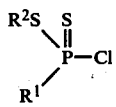

could be prepared analogously:

Table 1

| Compound | R¹ | R² | Method | Yield (% of theory) | Boiling point, °C./mm Hg |
|---|---|---|---|---|---|
| (ii) | $C_2H_5$ | $C_4H_9$-sec. | A | 82 | 100/4 |
|  |  |  | A | 52 | 100/7 |
| (iii) | $CH_3$ | $C_3H_7$-n | B | 54 | 120/16 |
| (iv) | $C_2H_5$ | $C_2H_5$ | A | 64 | 82/3 |
| (v) | $CH_3$ | $CH_3$ | A | 52 | 65/6 |

(b) 2nd reaction stage

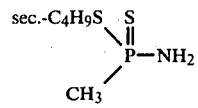

(vi)

30 g (0.15 mol) of S-sec.-butylmethanedithiophosphonic acid ester chloride were added dropwise, while stirring, to 150 ml of a technical-grade aqueous ammonia solution at 20°–30° C. The reaction mixture was then stirred for a further 30 minutes at 25° C., after which it was extracted by shaking twice with 150 ml of ether at a time; the layers were separated, and the combined organic phases were dried over magnesium sulphate and worked up further in the usual manner by distilling off the solvent. The volatile constituents which still remained were removed by "slight distillation" at a bath temperature of 80°–100° C./1 mm Hg. 24 g (87% of theory) of S-sec.-butylmethanedithiophosphonic acid ester-amide having a refractive index $n_D^{20}$ of 1.5715 remained.

The compounds of the following formula could be prepared analogously:

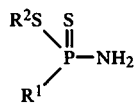

Table 2

| Compound | R¹ | R² | Yield (% of theory) |
|---|---|---|---|
| (vii) | $C_2H_5$ | $C_4H_9$-sec. | 87 |
| (viii) | $C_2H_5$ | $C_2H_5$ | 94 |
| (ix) | $CH_3$ | $C_3H_7$-n | 88 |

(c) 3rd reaction stage

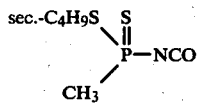

(x)

A mixture of 54 g (0.3 mol) of S-sec.-butylmethanedithiophosphonic acid ester-amide and 52.2 g (0.66 mol) of pyridine in 500 ml of anhydrous toluene was added dropwise at −40° C., while stirring, to a solution of phosgene in toluene, prepared from 180 ml of toluene and 30 g (0.33 mol) of phosgene at −40° C. The mixture was then warmed to about 25° C. in the course of two hours, the solids were filtered off and the filtrate was concentrated on a rotary evaporator under reduced pressure.

After distillation, 52 g (84% of theory) of S-sec.-butylmethanedithiophosphonic acid ester isocyanate of boiling point 92° C./5 mm Hg remained.

The compounds of the following formula could be prepared analogously:

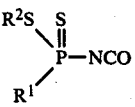

Table 3

| Compound | $R^1$ | $R^2$ | Yield (% of theory) | Boiling point, °C./mm Hg |
|---|---|---|---|---|
| (xi) | $C_2H_5$ | $C_4H_9$-sec. | 62 | 102/3 |
| (xii) | $C_2H_5$ | $C_2H_5$ | 59 | 90/4 |
| (xiii) | $CH_3$ | $C_3H_7$-n | 36 | 92/4 |

(d)

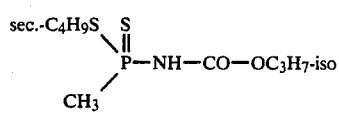
(I)

10.4 g (50 mmol) of S-sec.-butyl-methanedithiophosphonic acid ester isocyanate were added dropwise while stirring at room temperature to 100 ml of isopropanol, it being necessary to take care that the reaction temperature did not exceed 35° C. After stirring for one hour at room temperature, the solvent was removed on a rotary evaporator under reduced pressure and the residue was subjected to slight distillation at a bath temperature of 80°-100° C./1 mm Hg. 12.5 g (93% of theory) of S-sec.-butyl-N-iso-propoxycarbonylmethanedithiophosphonic acid ester-amide remained in the form of a yellow oil having a refractive index $n_D^{25}$ of 1.5303.

EXAMPLE 2

(a)

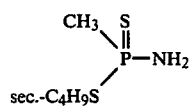

202.5 g (1 mol) of S-sec.-butylmethanedithiophosphonic acid chloride were added dropwise while stirring over the course of half an hour at 20°-30° C. (exothermic reaction) to 600 ml of a technical ammonia solution (about 10 mol); the mixture was then stirred further for one hour at room temperature after which 150 ml of toluene were added, the batch was stirred thoroughly and the phases were separated. The aqueous solution was extracted twice more with 150 ml of toluene at a time and the combined organic phases were dried over magnesium sulphate and then filtered. The solution thus obtained contained 0.9 mol (90% of theory) of S-sec.-butylmethanedithiophosphonic acid ester-amide and was directly processed further.

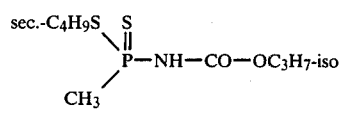
(1)

107 g (1.08 mol) of phosgene were passed into 700 ml of toluene at −5° to 0° C. A mixture of S-sec.-butylmethanedithiophosphonic acid ester-amide in toluene and 182 g (2.3 mol) of pyridine was then added dropwise to this solution over the course of one hour while stirring and cooling externally, in such a way that the internal temperature varied between 0° and 5° C. (strongly exothermic reaction), and the mixture was then stirred for a further hour without a cooling bath. In the course thereof, the reaction rose to about 15° C. 108 g (1.08 mol) of isopropanol (analytical grade) were now added dropwise to the mixture in the course of 15 minutes while stirring but without cooling, in the course of which the temperature rose to about 34° C.; the mixture was then warmed to 40° C. for 2 hours and cooled to room temperature, the precipitate was filtered off and rinsed with 250 ml of toluene, the filtrate was extracted by shaking twice with 250 ml of water at a time, and the phases were separated. The combined organic phases were dried over magnesium sulphate and filtered. The solvent was then stripped off on a rotary evaporator under reduced pressure. The residue was subjected to slight distillation for 1.5 hours at a bath temperature of 70° C./4 mm Hg. 220 g (91% of theory) of S-sec.-butyl-N-carbo-isopropoxy-methanedithiophosphonic acid ester-amide were obtained.

The following compounds of the formula

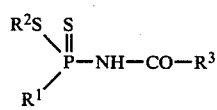
(I)

were prepared by analogous methods:

Table 4

| Compound No. | $R^1$ | $R^2$ | $R^3$ | Yield (% of theory) | Physical data (refractive index; melting point °C.) |
|---|---|---|---|---|---|
| 2 | $CH_3$ | $C_4H_9$-sec. | $OC_2H_5$ | 94 | $n_D^{21}$:1.5300 |
| 3 | $CH_3$ | $C_4H_9$-sec. | $NH-CH_3$ | 97 | 88-90 |
| 4 | $CH_3$ | $C_4H_9$-sec. | $N(CH_3)_2$ | 96 | 20 |
| 5 | $CH_3$ | $C_4H_9$-sec. | 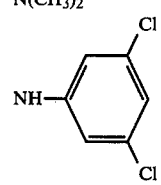 | 81 | 140-143 |
| 6 | $CH_3$ | $C_4H_9$-sec. | $OCH_3$ | 99 | $n_D^{23}$:1.5396 |
| 7 | $CH_3$ | $C_4H_9$-sec. | $OC_3H_7$-n | 97 | $n_D^{23}$:1.5280 |
| 8 | $CH_3$ | $C_4H_9$-sec. | $OC_4H_9$-tert. | 92 | $n_D^{23}$:1.5184 |
| 9 | $CH_3$ | $C_4H_9$-sec. | 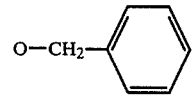 | 88 | |

Table 4-continued

| Compound No. | R¹ | R² | R³ | Yield (% of theory) | Physical data (refractive index; melting point °C.) |
|---|---|---|---|---|---|
| 10 | $CH_3$ | $C_4H_9$-sec. | 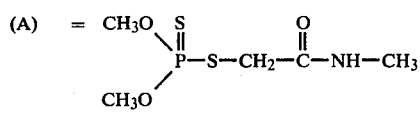 O— | 86 | $n_D^{23}$:1.5505 |
| 11 | $CH_3$ | $C_4H_9$-sec. | $O-CH_2-C\equiv CH$ | 91 | $n_D^{23}$:1.5399 |
| 12 | $CH_3$ | $C_4H_9$-sec. | $O-CH_2-CH=CH_2$ | 94 | $n_D^{23}$:1.5309 |
| 13 | $CH_3$ | $C_4H_9$-sec. | $NH-C_3H_7$-iso | 82 | 105 |
| 14 | $CH_3$ | $C_4H_9$-sec. | NH— (phenyl) | 73 | $n_D^{23}$:1.5846 |
| 15 | $CH_3$ | $C_4H_9$-sec. | $NH-CH_2-CH=CH_2$ | 90 | 60 |
| 16 | $C_2H_5$ | $C_2H_5$ | $OCH_3$ | 88 | $n_D^{23}$:1.5740 |
| 17 | $C_2H_5$ | $C_2H_5$ | $OC_3H_7$-iso | 91 | $n_D^{23}$:1.5510 |
| 18 | $C_2H_5$ | $C_2H_5$ | $OCH_2-C\equiv CH$ | 89 | $n_D^{23}$:1.5241 |
| 19 | $C_2H_5$ | $C_2H_5$ | $NH-CH_3$ | 94 | |
| 20 | $C_2H_5$ | $C_2H_5$ | $NH-C_3H_7$-iso | 88 | |
| 21 | $C_2H_5$ | $C_2H_5$ | $N(CH_3)_2$ | 91 | $n_D^{23}$:1.5420 |
| 22 | $C_2H_5$ | $C_2H_5$ | $OC_2H_5$ | 92 | $n_D^{20}$:1.5580 |
| 23 | $C_2H_5$ | $C_4H_9$-sec. | $OC_2H_5$ | 99 | $n_D^{23}$:1.5197 |
| 24 | $C_2H_5$ | $C_4H_9$-sec. | $OCH_3$ | 99 | $n_D^{23}$:1.5329 |
| 25 | $C_2H_5$ | $C_4H_9$-sec. | $OC_3H_7$-n | 95 | $n_D^{23}$:1.5179 |
| 26 | $C_2H_5$ | $C_4H_9$-sec. | $OC_3H_7$-iso | 74 | $n_D^{23}$:1.5141 |
| 27 | $C_2H_5$ | $C_4H_9$-sec. | $OC_4H_9$-tert. | 79 | $n_D^{23}$:1.5198 |
| 28 | $C_2H_5$ | $C_4H_9$-sec. | $O-CH_2-$ (phenyl) | 89 | $n_D^{23}$:1.5611 |
| 29 | $C_2H_5$ | $C_4H_9$-sec. | $O-CH_2-C\equiv CH$ | 95 | $n_D^{23}$:1.5422 |
| 30 | $C_2H_5$ | $C_4H_9$-sec. | $O-CH_2-CH=CH_2$ | 94 | $n_D^{23}$:1.5327 |
| 31 | $C_2H_5$ | $C_4H_9$-sec. | $NH-CH_3$ | 94 | ~93 |
| 32 | $C_2H_5$ | $C_4H_9$-sec. | $N(CH_3)_2$ | 84 | 67 |
| 33 | $C_2H_5$ | $C_4H_9$-sec. | $NH-C_3H_7$-iso | 94 | 70 |
| 34 | $C_2H_5$ | $C_4H_9$-sec. | NH— (phenyl) | 99 | 30 |
| 35 | $C_2H_5$ | $C_4H_9$-sec. | $NH-CH_2-CH=CH_2$ | 95 | $n_D^{23}$:1.5435 |
| 36 | $CH_3$ | $C_3H_7$-n | $OCH_3$ | 88 | $n_D^{21}$:1.5512 |
| 37 | $CH_3$ | $C_3H_7$-n | $OC_2H_5$ | | |
| 38 | $CH_3$ | $C_3H_7$-n | $OC_3H_7$-iso | 85 | $n_D^{21}$:1.5305 |
| 39 | $CH_3$ | $C_3H_7$-n | $O-CH_2-CH_2-OCH_3$ | 96 | $n_D^{21}$:1.5240 |
| 40 | $CH_3$ | $C_3H_7$-n | $NH_2$ | | |
| 41 | $CH_3$ | $C_3H_7$-n | $NH-CH_3$ | 97 | 87 |
| 42 | $CH_3$ | $C_3H_7$-n | $N(CH_3)_2$ | 83 | 57 |
| 43 | $CH_3$ | $C_3H_7$-n | $NH-C_3H_7$-iso | 95 | 68 |
| 44 | $CH_3$ | $C_3H_7$-n | NH— (phenyl) | | |
| 45 | $CH_3$ | $C_3H_7$-n | $SC_2H_5$ | 93 | $n_D^{21}$:1.5738 |
| 46 | $CH_3$ | $C_3H_7$-n | $SC_3H_7$-n | | |

The insecticidal, acaricidal and nematicidal activity of the compounds of this invention is illustrated by the following examples wherein the compounds according to the present invention are each identified by the number (given in brackets) from the preparative examples hereinabove.

The known comparison compounds are identified as follows:

(A) = $CH_3O$–P(=S)(–$OCH_3$)–S–$CH_2$–C(=O)–NH–$CH_3$ (B) = $CH_3O$–P(=O)(–$SCH_3$)–NH–C(=O)–$CH_3$

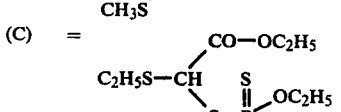

(C) = $C_2H_5S$–CH(–CO–$OC_2H_5$)–S–P(=S)(–$OC_2H_5$)–NH–$C_3H_7$-iso (D) = $C_2H_5S$–CH(–CO–$OC_2H_5$)–S–P(=O)(–$OC_2H_5$)–NH–$C_4H_9$-sec.

-continued (E) = 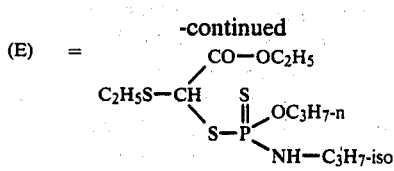

EXAMPLE 3

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all of the flies were killed; 0% meant that none of the flies were killed.

The active compounds, the concentrations of the active compounds, the evaluation times and the results can be seen from the following table:

Table 5

| Active compound | (Drosophila Test) Active compound concentration in % | Degree of destruction in % after 1 day |
|---|---|---|
| (A) | 0.01 | 100 |
|  | 0.001 | 0 |
| (B) | 0.01 | 0 |
| (2) | 0.01 | 100 |
|  | 0.001 | 95 |
| (1) | 0.01 | 100 |
|  | 0.001 | 100 |
| (8) | 0.01 | 100 |
|  | 0.001 | 100 |
| (23) | 0.01 | 100 |
|  | 0.001 | 90 |
| (26) | 0.01 | 100 |
|  | 0.001 | 98 |
| (27) | 0.01 | 100 |
|  | 0.001 | 100 |

EXAMPLE 4

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 6

| Active compound | (Phaedon larvae test) Active compound concentration in % | Degree of destruction in % after 3 days |
|---|---|---|
| (B) | 0.1 | 100 |
|  | 0.01 | 20 |
| (6) | 0.1 | 100 |
|  | 0.01 | 100 |
| (5) | 0.1 | 100 |
|  | 0.01 | 100 |
| (24) | 0.1 | 100 |
|  | 0.01 | 100 |
| (34) | 0.1 | 100 |
|  | 0.01 | 100 |
| (36) | 0.1 | 100 |
|  | 0.01 | 100 |
| (38) | 0.1 | 100 |
|  | 0.01 | 100 |

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 7

| Active compound | (Tetranychus test/resistant) Active compound concentration in % | Degree of destruction in % after 2 days |
|---|---|---|
| (B) | 0.1 | 0 |
| (9) | 0.1 | 100 |
| (6) | 0.1 | 100 |
| (2) | 0.1 | 100 |
| (7) | 0.1 | 100 |
| (1) | 0.1 | 100 |
| (12) | 0.1 | 100 |
| (11) | 0.1 | 100 |
| (8) | 0.1 | 100 |
| (10) | 0.1 | 98 |
| (3) | 0.1 | 100 |
| (4) | 0.1 | 100 |
| (13) | 0.1 | 100 |
| (14) | 0.1 | 100 |
| (25) | 0.1 | 98 |
| (26) | 0.1 | 98 |
| (27) | 0.1 | 99 |
| (36) | 0.1 | 100 |
| (38) | 0.1 | 100 |
| (43) | 0.1 | 100 |

EXAMPLE 6

Root-systemic action
  Test insect: *Phaedon cochleariae* larvae
  Solvent: 3 parts by weight of acetone
  Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

The active compounds, the amounts used and the results can be seen from the following table:

Table 8

| Root-systemic action (*Phaedon cochleariae* larvae) | |
|---|---|
| Active compound | Degree of destruction in % at an active compound concentration of 5 ppm |
| (C) | 0 |
| (D) | 0 |
| (E) | 0 |
| (23) | 100 |
| (24) | 100 |
| (25) | 100 |
| (26) | 100 |
| (29) | 100 |
| (30) | 100 |

| Critical concentration test/root-systemic action (*Phaedon cochleariae* larvae) | |
|---|---|
| Active compound | Degree of destruction in % at an active compound concentration of 5 ppm |
| (6) | 100 |
| (33) | 100 |

EXAMPLE 7

Root-systemic action
  Test insect *Myzus persicae*
  Solvent: 3 parts by weight of acetone
  Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

The active compounds, the amounts used and the results can be seen from the following table:

Table 9

| Root-systemic action (*Myzus persicae*) | |
|---|---|
| Active compound | Degree of destruction in % at an active compound concentration of 5 ppm |
| (C) | 0 |
| (D) | 0 |
| (E) | 0 |
| (24) | 100 |
| (6) | 100 |
| (7) | 100 |

EXAMPLE 8

Test nematode: *Meloidogyne incognita*
  Solvent: 3 parts by weight of acetone
  Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 10

| Active compound | *Meloidogyne incognita)* Degree of destruction in % at an active compound concentration of 5 ppm |
|---|---|
| (C) | 0 |
| (D) | 0 |
| (E) | 0 |
| (4) | 100 |
| (1) | 100 |
| (23) | 100 |
| (24) | 100 |
| (25) | 100 |
| (26) | 100 |
| (29) | 100 |
| (30) | 100 |
| (27) | 100 |
| (33) | 100 |
| (6) | 100 |
| (7) | 100 |
| (8) | 100 |
| (13) | 100 |
| (31) | 100 |

EXAMPLE 9

Test insects: *Sitophilus granarius*
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 11

| | *Sitophilus granarius* | |
|---|---|---|
| Active compounds | Active compound concentration of the solution in % | Destruction (%) after 3 days |
| (36) | 0.02 | 100 |
| (38) | 0.02 | 100 |
| (45) | 0.02 | 100 |
| (42) | 0.02 | 100 |

It will be appreciated that the instant specification and examples are set forth by way of illustration and not limitation, and that various modifications and changes may be made without departing from the spirit and scope of the present invention.

What is claimed is:

1. An S-alkyl-β-carbonylalkanedithiophosphonic acid ester-amide of the formula

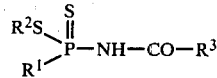

in which
R¹ is alkyl with 1 to 5 carbon atoms,
R² is alkyl with 1 to 6 carbon atoms, and
R³ is alkoxy or alkylthio with 1 to 6 carbon atoms, alkenyloxy or alkynyloxy each with up to 6 carbon atoms, alkoxyalkoxy with 1 to 3 carbon atoms in each alkoxy moiety, phenyloxy, halogenophenoxy, benzyloxy, monoalkylamino with 1 to 6 carbon atoms, dialkylamino with 1 or 2 carbon atoms per alkyl radical, phenylamino, chlorophenylamino, or alkylamino.

2. A compound according to claim 1, wherein such compound is S-sec.-butyl-N-iso-propoxycarbonyl-methanedithiophosphonic acid ester-amide of the formula

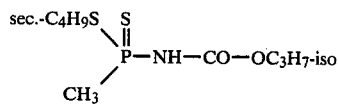

3. A compound according to claim 1, wherein such compound is S-sec.-butyl-N-ethoxycarbonyl-methanedithiophosphonic acid ester-amide of the formula

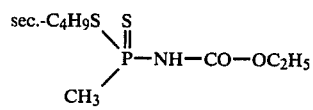

4. A compound according to claim 1, wherein such compound is S-sec.-butyl-N-methoxycarbonyl-methanedithiophosphonic acid ester-amide of the formula

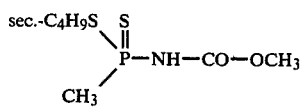

5. A compound according to claim 1, wherein such compound is S-sec.-butyl-N-n-propoxycarbonyl-methanedithiophosphonic acid ester-amide of the formula

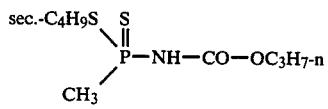

6. A compound according to claim 1, wherein such compound is S-sec.-butyl-N-methoxycarbonyl-ethanedithiophosphonic acid ester-amide of the formula

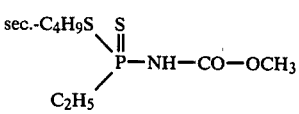

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes, or to a habitat thereof an arthropodicidally or nematicidally effective amount of a compound according to claim 1.

9. The method according to claim 8 in which said compound is

S-sec.-butyl-N-iso-propoxycarbonyl-methanedithiophosphonic acid ester-amide,

S-sec.-butyl-N-ethoxycarbonyl-methanedithiophosphonic acid ester-amide,

S-sec.-butyl-N-methoxycarbonyl-methanedithiophosphonic acid ester-amide,

S-sec.-butyl-N-n-propoxycarbonyl-methanedithiophosphonic acid ester-amide, or

S-sec.-butyl-N-methoxycarbonyl-ethanedithiophosphonic acid ester-amide.

* * * * *